United States Patent [19]

Hilfman

[11] 4,148,759

[45] Apr. 10, 1979

[54] HYDROCARBON CONVERSION CATALYTIC COMPOSITE

[75] Inventor: Lee Hilfman, Mt. Prospect, Ill.

[73] Assignee: UOP Inc., Des Plaines, Ill.

[21] Appl. No.: 810,323

[22] Filed: Jun. 27, 1977

Related U.S. Application Data

[63] Continuation-in-part of Ser. No. 684,055, May 6, 1976, abandoned.

[51] Int. Cl.$^2$ .................. B01J 29/06; C10G 13/02
[52] U.S. Cl. ............................. 252/455 Z; 208/111
[58] Field of Search .................. 252/455 Z; 208/111

[56] References Cited

U.S. PATENT DOCUMENTS

| | | | |
|---|---|---|---|
| 3,172,835 | 3/1965 | Scott, Jr. | 208/111 X |
| 3,297,564 | 1/1967 | Peck et al. | 208/111 |
| 3,365,392 | 1/1968 | Mitsche et al. | 252/455 Z |
| 3,709,814 | 1/1973 | Jaffe | 252/455 Z |

*Primary Examiner*—Carl Dees

*Attorney, Agent, or Firm*—James R. Hoatson, Jr.; John G. Cutts, Jr.; William H. Page, II

[57] ABSTRACT

A catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum. The key feature of the subject composite is the criticality of the platinum content of the composite. The principal utility of the subject composite is in the conversion of hydrocarbon feed stocks and in particular the hydrocracking of hydrocarbons. A specific example of the catalyst disclosed is a combination of nickel, molybdenum and platinum with a high silica faujasite-alumina carrier material containing 25 weight percent alumina in amounts sufficient to result in the composite containing, on an elemental basis, about 1 to about 15 weight percent nickel, about 1 to about 10 weight percent molybdenum and about 0.2 to about 0.5 weight percent platinum.

3 Claims, 1 Drawing Figure

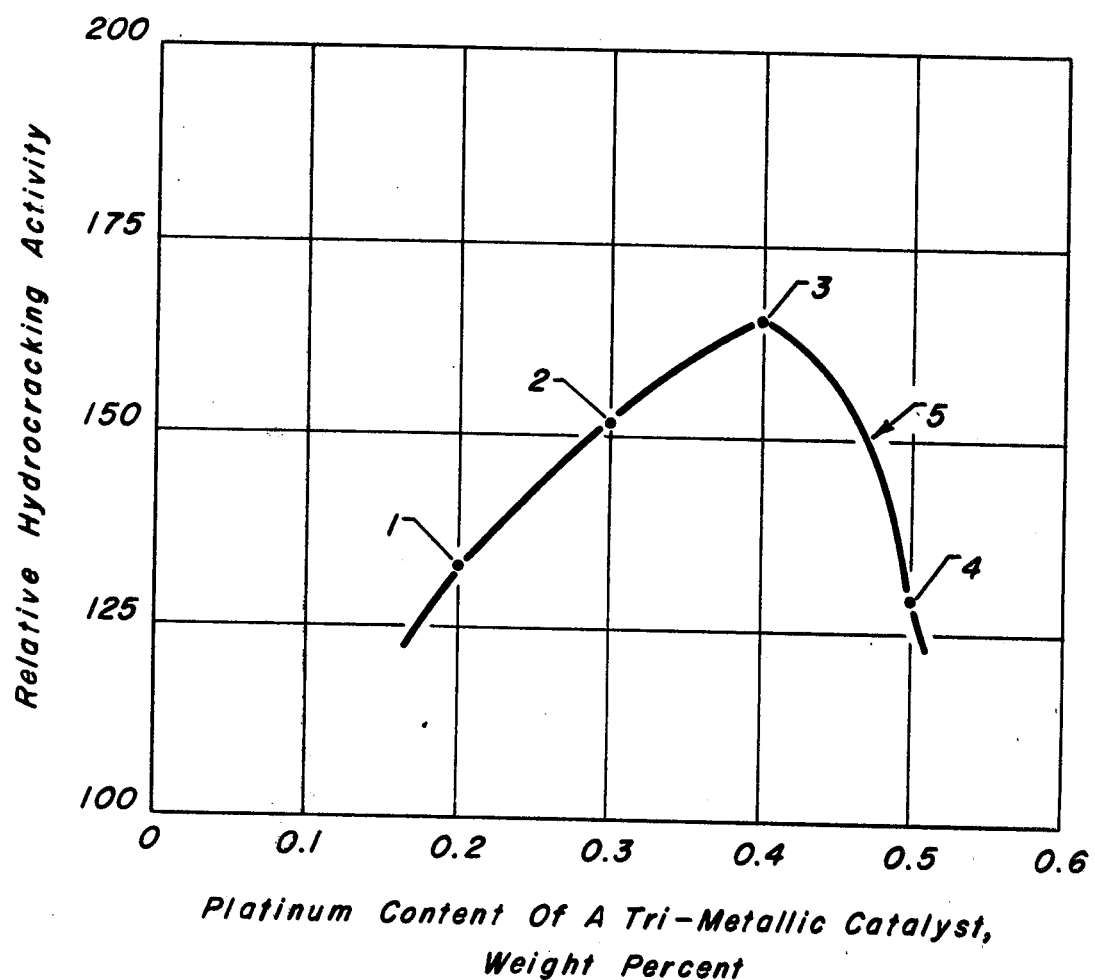

HYDROCARBON CONVERSION CATALYTIC COMPOSITE

CROSS-REFERENCE TO RELATED APPLICATION

This application is a continuation-in-part of my prior, copending application Ser. No. 684,055 filed on May 6, 1976, now abandoned. All of the teachings of this prior application are specifically incorporated herein by reference thereto.

The subject of the present invention is a novel catalytic composite which has exceptional activity, selectivity and resistance to deactivation when employed in a hydrocarbon conversion process. This invention also relates to the preparation of a novel catalytic composite. More particularly, the invention relates to a catalyst which is useful for performing destructive hydrogenation or hydrocracking of hydrocarbons.

Destructive hydrogenation by catalytic means, more commonly called hydrocracking, is old and well-known to the art. Hydrocracking of the hydrocarbon oil, which is usually a coal tar or a high-boiling petroleum fraction, such as gas oils or topped crude, generally is performed at relatively high temperatures and pressures of the order of 700° F. and 1500 psig. and upward. Catalysts for the destructive hydrogenation of hydrocarbons are generally a combination of hydrogenation and cracking catalysts.

While many types of catalyst compositions have been proposed for hydrocracking, it has been found that catalysts comprised of silica, alumina, Group VIB and VIII metals are especially suitable. Such catalysts are well known in the hydrocracking art.

However, because commercial sale hydrocracking of hydrocarbons is performed at low space velocities, catalyst cost is an appreciable factor in both the initial investment and operating costs of hydrocracking plants. For this reason, there is considerable incentive to manufacture catalysts which exhibit the greatest activity and stability. I have discovered an improved catalyst comprising nickel-molybdenum-platinum on a zeolitic support or carrier material. More specifically, I have discovered that an unusually superior catalyst results if the platinum content is from about 0.2 to about 0.5 weight percent on an elemental basis. The criticality of the range of the platinum concentration is further illustrated hereinbelow.

A particularly preferred catalyst support or base comprises a zeolite and alumina. In addition to the foregoing compositional limitations, it is important that the catalyst base have adequate pore volume, that is, a pore volume of at least 0.5 cc/g and preferably at least 0.6 cc/g or even 0.7 cc/g.

The zeolite-alumina catalyst base is preferably in the zerogel state, that is, it is dried sufficiently to afford the usual microporous structure and therefore an appreciable available surface.

The catalyst of the present invention can be utilized to achieve the maximum production of LPG (liquefied petroleum gas) in the propane/butane range from naptha or gasoline boiling range distillates. Heavier charge stocks, including kerosenes, light gas oils, heavy gas oils, full boiling range gas oils and "black oils" may be readily converted into lower-boiling normally liquid products including gasolines, kerosenes, middle distillates, lube oils, etc.

In one embodiment accordingly, the present invention provides a method of preparing catalytic composites having hydrocracking activity comprising the steps: (a) preparing a zeolite-alumina carrier material; (b) impregnating said zeolite-alumina carrier material with a nickel component, a molybdenum component and a platinum component in amounts sufficient to result in the composite containing, on an elemental basis, about 1 to about 15 weight percent nickel, about 1 to about 10 weight percent molybdenum and about 0.2 to about 0.5 weight percent platinum.

In a second embodiment, the present invention relates to a process for hydrocracking hydrocarbons which process comprises reacting said hydrocarbons with hydrogen in a reaction zone containing a catalytic composite prepared by a method comprising the steps: (a) preparing a zeolite-containing carrier material; (b) impregnating said carrier material with a nickel component, a molybdenum component and a platinum component in amounts sufficient to result in the composite containing, on an elemental basis, about 1 to about 15 weight percent nickel, about 1 to about 10 weight percent molybdenum and about 0.2 to about 0.5 weight percent platinum.

In a specific embodiment, the hydrocracking conditions include a maximum catalyst bed temperature of about 600° F. to about 900° F., a pressure of about 500 to about 5000 psig., a liquid hourly space velocity of about 0.1 to about 10 and a hydrogen circulation rate in the range of about 1000 to about 50,000 scf./bbl.

Other objects and embodiments of my invention relate to additional details regarding the prepared catalytic ingredients, the concentration of components within the catalytic composite, the method of catalyst preparation, preferred processing techniques and similar particulars which are hereinafter set forth.

Catalytic compositions, tailored for the conversion of hydrocarbonaceous material and particularly those intended for utilization in a hydrocracking process, have traditionally consisted of metallic elements chosen from Group VIII of the Periodic Table; however, metallic components from Group VIB are quite often incorporated therein. In those instances where hydrocracking is intended to be accompanied by some hydrorefining (desulfurization, denitrification, etc.) the preferred metallic components have been nickel and molybdenum, and nickel and tungsten, which components are usually combined with a porous carrier material comprising both alumina and silica, either amorphous or zeolitic in nature. Ample evidence may be found in the literature which confirms the ability of the nickel component to effect both cracking and hydrogenation reactions.

I have found that a particularly effective zeolite-nickel-molybdenum-platinum hydrocracking catalyst can be prepared when the platinum content of the finished catalyst is maintained within the critical range of from about 0.2 to about 0.5 weight percent. Thus, it is now possible to prepare a more active and stable hydrocracking catalyst.

As is customary in the art of catalysis, when referring to the catalytically active metal, or metals, it is intended to encompass the existence of such metal in the elemental state or in some form such as an oxide, sulfide, halide, etc. Regardless of the state in which the metallic components actually exist, the concentrations are computed as if they existed in the elemental state.

The zeolite carrier material may be prepared and utilized as spheres, pills, pellets, extrudates, granules, etc. The carrier material may be prepared in any suitable manner and may be activated prior to use by one or more treatments including drying, calcination, steaming, etc. Although generally existing in some combined form, the concentration of the catalytically active metallic components is calculated on the basis of the elemental metals. Suitable hydrocracking catalysts will contain from about 0.01% to about 30% by weight of one or more metals, or compounds thereof. Another constituent of hydrocracking catalysts is a halogen component. While the precise form of association of the halogen component of the carrier material is not accurately known, it is customary in the art to refer to the halogen component as being combined with the carrier or with the other ingredients of the catalyst therein. Combined halogen may be either fluorine, chlorine, iodine, bromine or mixtures thereof; of these, fluorine and chlorine are particularly preferred. The halogen will be composited with the carrier material in such a manner as results in a final catalytic composite containing from about 0.1% to about 2% by weight of a halogen component, calculated as the element.

The metallic components may be incorporated within the catalytic composite in any suitable manner including ion-exchange or impregnation of the carrier, and either after or before calcination. The preferred method for the incorporation of the metallic components is to impregnate the carrier material with an aqueous solution of nickel and molybdenum salts and then after drying and calcining, the platinum component is added with a separate impregnation with an aqueous solution of a chloroplatinic acid. Although the metallic components may be incorporated in any manner, it is believed that the two-step impregnation method hereinabove described yields a superior hydrocracking catalyst. Even though the reasons for such a superior catalyst are uncertain, it is believed that the incorporation of the platinum metal component subsequent to the incorporation of the molybdenum component results in the construction of the most favorable metallic clusters utilized in hydrocracking reactions.

Following the incorporation of the metallic components, the carrier material is dried and subjected to a high temperature calcination or oxidation technique at a temperature of about 750° F. to about 1000° F. One particularly preferred catalyst preparation technique involves the water-free reduction of the calcined composite. This particular step is designed to insure a more uniform and finely divided dispersion of the metallic components throughout the carrier material. Substantially pure and dry hydrogen, containing less than 30 volume ppm. of water is utilized as the reducing agent. The reduced catalytic composite is then subjected to a presulfiding technique to incorporate from about 0.05% to about 3.0% by weight of sulfur, on an elemental basis, within the final catalytic composite.

The catalyst composite, prepared in accordance with the method of this invention, is preferably employed in a reaction zone as a fixed bed. The hydrocarbon charge stock after being combined with hydrogen in an amount of from about 2000 to about 20,000 standard cubic feet per barrel, and preferably at least about 5000 standard cubic feet per barrel, is introduced into the reaction zone. The charge stock may be in a liquid, or liquid-vapor phase mixture, depending upon the temperature, pressure, proportion of hydrogen and the boiling range of the charge stock being processed. The liquid hourly space velocity through the reaction zone will be in excess of about 0.2 and generally in the range of from about 1 to about 15. The source of hydrogen being admixed with a hydrocarbon charge stock may comprise a hydrogen-rich gas stream which is withdrawn from a high-pressure, low-temperature separation zone and recycled to supply at least a portion of such hydrogen. Excess hydrogen resulting from the various dehydrogenation reactions effected in a catalytic reforming unit may also be employed in admixture with the hydrocarbon charge. The reaction zone will operate under an imposed pressure within the range of from about 80 to about 3000 psig. The catalyst bed inlet temperature is maintained within the range of from about 350° to about 800° F. Since the hydrocracking reactions are exothermic, the outlet temperature or the temperature at the bottom of the catalyst bed will be significantly higher than that at the inlet thereto. The degree of exothermicity exhibited by the temperature rise across the catalyst bed is at least partially dependent upon the character of the charge stock passing therethrough, the rate at which the normally liquid hydrocarbon charge contacts the catalyst bed, the intended degree of conversion to lower-boiling hydrocarbon products, etc. In any event, the catalyst bed inlet temperature will be such that the exothermicity of the reactions taking place does not cause the temperature at the outlet of the bed to exceed about 900° F., and preferably 850° F. The operation may also be effected as a moving-bed type, or suspensoid type of operation in which the catalyst, hydrocarbon and hydrogen are admixed and passes as a slurry through the reaction zone.

Although the method of preparing the catalyst, and careful selection of operating conditions within the ranges hereinbefore set forth, extend the effective life of the catalyst composite, regeneration thereof may eventually become desired due to the natural deterioration of the catalytically active metallic components. The catalytic composite is readily regenerated by treating the same in an oxidizing atmosphere, at a temperature of from about 750° F. to about 850° F., and burning coke and other heavy hydrocarbonaceous material therefrom. The catalyst composite may then be subjected to the reducing in hydrogen, in situ, at a temperature up to about 1000° F. If desirable, the catalyst may then be sulfided in the same manner as fresh catalyst as hereinbefore described.

The drawing included in the instant application is for the purpose of visually demonstrating the improvements and advantages afforded by the manufacture of zeolite-nickel-molybdenum-platinum hydrocracking catalyst according to the present invention.

The following examples are presented in illustration of the catalyst of this invention and is not intended as an undue limitation on the generally broad scope of the invention as set out in the appended claims.

EXAMPLE I

This example describes the preparation and testing of four zeolite-nickel-molybdenum-platinum catalysts each of which has an extruded carrier material containing 25% alumina and 75% faujasite, 5% nickel, 2% molybdenum and which contain 0.2, 0.3, 0.4 and 0.5 weight percent platinum, respectively. The extruded alumina-faujasite carrier material was initially impregnated with an aqueous solution containing soluble nickel and molybdenum salts in sufficient concentration to yield a finished catalyst with the desired nickel and molybdenum concentrations. The freshly impregnated support was then dried at about 100° C. and calcined at about 500° C. The resulting dried and calcined carrier material containing 5% nickel and 2% molybdenum was divided into five batches and four batches were impregnated with an aqueous chloroplatinic acid solution with a concentration sufficient to yield a finished catalyst with 0.2, 0.3, 0.4 and 0.5 weight percent platinum, respectively. The platinum impregnated catalysts were then dried and calcined at 100° C. and 500° C., respectively. The fifth batch was not impregnated with platinum and served as a reference catalyst for comparison purposes.

A portion of each of the five hereinabove described batches of catalyst was then used in the hydrocracking of a vacuum gas oil whose properties are summarized in Table I.

TABLE I

| PROPERTIES OF VACUUM GAS OIL | |
|---|---|
| API° Gravity at 60° F. | 33.5 |
| Distillation, ° F. | |
| IBP | 290 |
| 10 | 455 |
| 30 | 596 |
| 50 | 697 |
| 70 | 762 |
| 90 | 830 |
| 95 | 870 |
| E.P. | 930 |
| % Over | 99 |
| Total Sulfur, wt. % | 0.22 |
| Total Nitrogen, ppm. | 3 |

In each case, the vacuum gas oil was processed with a reactor pressure of 1500 psig., a liquid hourly space velocity of 2.0, a hydrogen circulation rate of 10,000 scf./bbl. and at a peak catalyst bed temperature of 315° C.

The hydrocracking ability of the non-platinum containing reference catalyst was arbitrarily assigned a Relative Hydrocracking Activity of 100. Platinum containing catalysts comprising 0.2, 0.3, 0.4 and 0.5 weight percent platinum and hereinafter referred to as Catalysts 1, 2, 3, and 4, respectively, were utilized to hydrocrack the hereinbefore described vacuum gas oil and these four catalysts exhibited a Relative Hydrocracking Activity of 133, 152, 165, and 129, respectively. These data are presented in tabular form in Table II and in graphical form in the accompanying drawing.

TABLE II

| EVALUATION FOR HYDROCRACKING ACTIVITY | | | | |
|---|---|---|---|---|
| Catalyst Identity | 1 | 2 | 3 | 4 |
| Platinum Concentration, wt. % | 0.2 | 0.3 | 0.4 | 0.5 |
| Relative Hydrocracking Activity | 133 | 152 | 165 | 129 |

From the data presented in foregoing Table II and with reference to the accompanying drawing, it will be seen that the four catalysts' increasing concentrations of platinum, the latter ranging from 0.2% to 0.5% by weight, did not demonstrate linearly increasing Relative Hydrocracking Activity. This is clearly brought out upon comparing the results obtained through the use of Catalysts 1, 2, 3 and 4 which indicated a Relative Hydrocracking Activity of 133, 152, 165 and 129 respectively, for the conversion of vacuum gas oil to lower boiling hydrocarbons. Datum points 1, 2, 3 and 4 in the drawing are representative of the results obtained with Catalysts 1, 2, 3 and 4, respectively. These data were employed in preparing curve 5 of the drawing, which curve clearly illustrates the criticality attached to the platinum concentration within the range of about 0.2% to about 0.5% by weight, in order to produce a hydrocracking catalyst with superior performance characteristics. The additional economic advantages afforded through this particular result will be readily recognized by those possessing skill within the art of petroleum refining processes.

EXAMPLE II

This example describes the preparation and testing of three zeolite-nickel-molybdenum-platinum catalysts each of which has an extruded carrier material containing 25% alumina and 75% faujasite, 5% nickel, 2% molybdenum and which contain 0.2 wt. % platinum, 0.5 wt. % platinum and 0.4 wt. % palladium, respectively. The extruded alumina-faujasite carrier material was prepared in exactly the same manner as hereinabove described in Example I. The 5% nickel and 2% molybdenum was incorporated with said carrier material, also, as hereinabove described in Example I. Two portions of the resulting dried and calcined carrier material containing 5% nickel and 2% molybdenum were impregnated with an aqueous chloroplatinic acid solution with a concentration sufficient to yield a finished catalyst with 0.2 and 0.5 wt. % platinum, respectively. A third portion of the dried and calcined carrier material containing 5% nickel and 2% molybdenum was impregnated with an aqueous solution containing palladium chloride with a concentration sufficient to yield a finished catalyst with 0.4 wt. % palladium. Each of the three portions of the impregnated catalysts were then dried and calcined at 100° C. and 500° C., respectively.

The three portions of catalyst prepared as hereinabove described were then used in the hydrocracking of a vacuum gas oil whose properties are summarized in Table I. In each case, the gas oil was processed with a reactor pressure of 1500 psig., a liquid hourly space velocity of 2.0, a hydrogen circulation rate of 10,000 scf./bbl. and at a peak catalyst bed temperature of 325° C. It will be noted that catalyst bed temperature of Example I was 315° C.

The hydrocracking ability of the non-platinum and non-palladium reference catalyst of Example I was arbitrarily assigned a Relative Hydrocracking Activity of 100. Platinum containing catalysts comprising 0.2 and 0.5 wt. % platinum and palladium containing catalyst comprising 0.4 wt. % palladium hereinafter referred to as Catalysts 5, 6 and 7, respectively, were utilized to hydrocrack the hereinbefore described vacuum gas oil and these three catalysts exhibited a Relative Hydrocracking Activity of 141, 163 and 105, respectively. These data are presented in tabular form in Table III.

TABLE III

| Evaluation for Hydrocracking Activity | | | |
|---|---|---|---|
| Catalyst Identity | 5 | 6 | 7 |
| Platinum Concentration, wt. % | 0.2 | 0.5 | — |
| Palladium Concentration, wt. % | — | — | 0.4 |
| Relative Hydrocracking Activity | 141 | 163 | 105 |

The data presented in foregoing Table III illustrate that a platinum containing catalyst in the claimed critical range, viz., about 0.2 to about 0.5 wt.%, exhibits unexpected and greatly superior catalytic activity when compared with a catalyst containing palladium within the same range. When a Relative Activity comparison of 163 versus 105 can be demonstrated in the realm of catalysis, those skilled in the art will readily recognize the economic advantages afforded through the catalyst of the present invention and the fact that a randomly selected component from a Group VIII or any other group will not necessarily exhibit the desired catalytic characteristics.

The foregoing specification and example clearly illustrate the improvements encompassed by the present invention and the benefits to be afforded a process for the hydrocracking of hydrocarbons.

I claim as my invention:

1. A catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum.

2. A catalytic composite as defined in claim 1 wherein said zeolitic carrier material comprises faujasite and alumina.

3. A catalytic composite as defined in claim 1 wherein said zeolitic carrier material contains 25% by weight alumina and 75% by weight faujasite.

* * * * *